United States Patent [19]
Button et al.

[11] Patent Number: 5,304,130
[45] Date of Patent: Apr. 19, 1994

[54] CONTAINER FOR THE CONTROLLED ADMINISTRATION OF A BENEFICIAL AGENT

[75] Inventors: Kathryn M. Button, Ingleside; Steven C. Jepson, Palatine; Birendra K. Lal, Glendale Heights; Douglas W. Reitz, Arlington Heights; James Richardson, Schaumburg; Richard A. Rollins, Mundelein; Paul J. Soltys, Lake Zurich; Thomas E. Dudar, Palatine, all of Ill.

[73] Assignee: Baxter International Inc., Deerfield, Ill.

[21] Appl. No.: 841,957

[22] Filed: Feb. 26, 1992

[51] Int. Cl.$^5$ .............................. A61M 37/00
[52] U.S. Cl. ............................. 604/85; 604/82; 604/409; 604/410; 604/416
[58] Field of Search ................... 604/82-85, 604/410, 408, 409, 414, 416, 403, 415, 43, 92, 56; 222/211, 476

[56] References Cited

U.S. PATENT DOCUMENTS

| | | |
|---|---|---|
| 4,325,368 | 4/1982 | Kaemmerer .................. 604/82 |
| 4,381,776 | 5/1983 | Latham, Jr. . |
| 4,465,471 | 8/1984 | Harris et al. . |
| 4,534,757 | 8/1985 | Geller . |
| 4,573,967 | 3/1986 | Hargrove et al. . |
| 4,735,608 | 4/1988 | Sardam .................. 604/82 |
| 4,804,366 | 2/1989 | Zdeb et al. . |
| 4,832,690 | 5/1989 | Kuu . |
| 4,874,366 | 10/1989 | Zdeb et al. . |
| 4,936,829 | 6/1990 | Zdeb et al. . |
| 5,024,657 | 6/1991 | Needham et al. . |
| 5,030,203 | 7/1991 | Wolf, Jr. et al. . |
| 5,049,129 | 9/1991 | Zdeb et al. . |
| 5,074,844 | 12/1991 | Zdeb et al. . |

FOREIGN PATENT DOCUMENTS

| | | |
|---|---|---|
| 2105695 | 3/1983 | United Kingdom . |
| 8904654 | 6/1989 | World Int. Prop. O. . |
| 8904687 | 6/1989 | World Int. Prop. O. . |
| 8904689 | 6/1989 | World Int. Prop. O. . |
| 8906553 | 7/1989 | World Int. Prop. O. . |

*Primary Examiner*—John D. Yasko
*Assistant Examiner*—Ronald K. Stright, Jr.
*Attorney, Agent, or Firm*—Paul E. Schaafsma; Amy L. H. Rockwell; Paul C. Flattery

[57] ABSTRACT

A container for housing a beneficial agent that can be removably coupled to a structure defining a fluid flow path. The container comprises a body defining a first and second interior area separated by a wall that terminates at an opening providing fluid communication between the first and second interior area. A cannula is provided that extends from the body for being removably received by the structure defining the fluid path. The cannula includes an inlet opening and inlet fluid flow path and an outlet opening and outlet fluid flow path. The inlet fluid flow path being in fluid communication with the first interior area, and the outlet fluid flow path being in fluid communication with the second interior area. The second interior area houses the solid beneficial agent and allows fluid that flows through the inlet fluid flow path to pass by at least a portion of the beneficial agent.

29 Claims, 5 Drawing Sheets

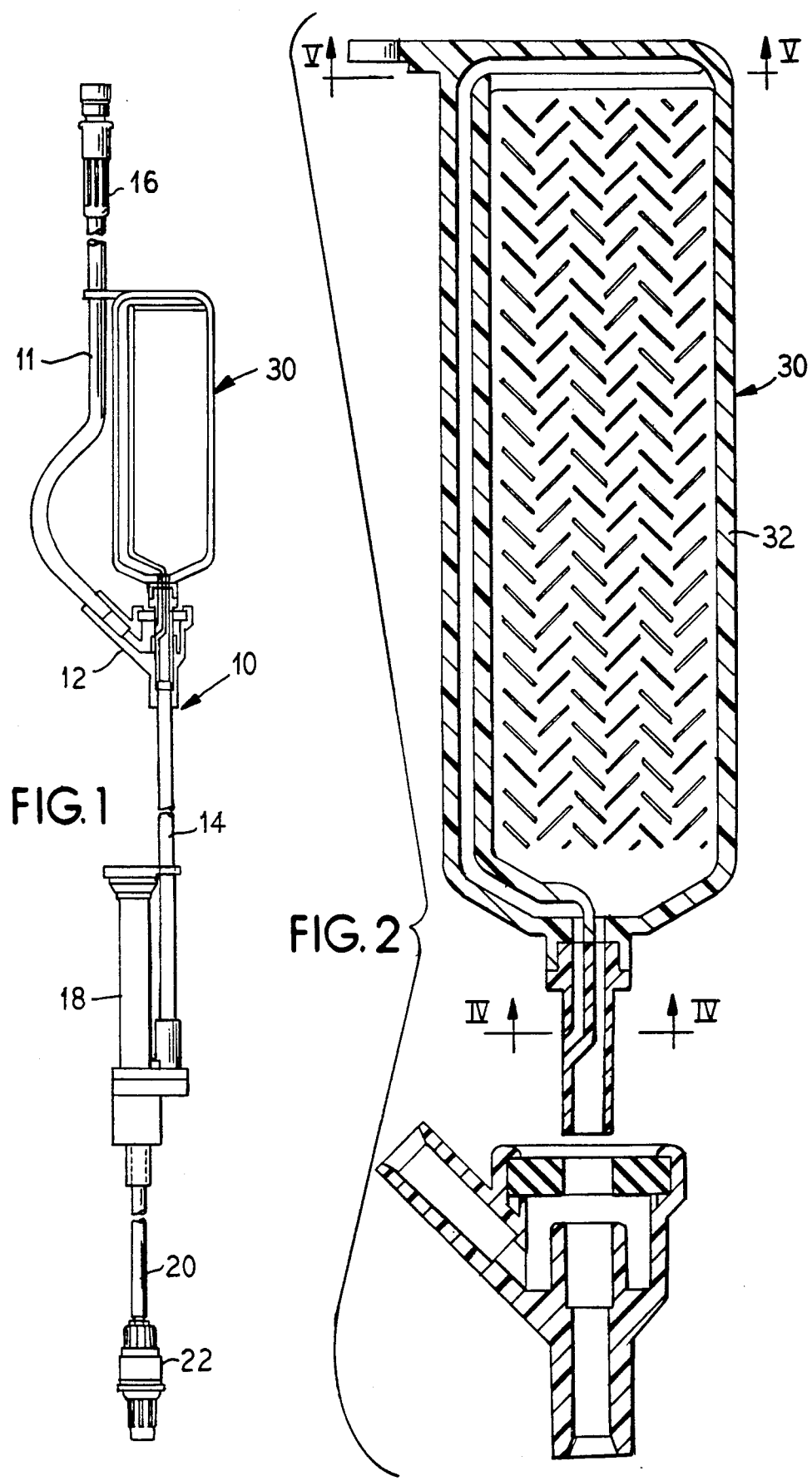

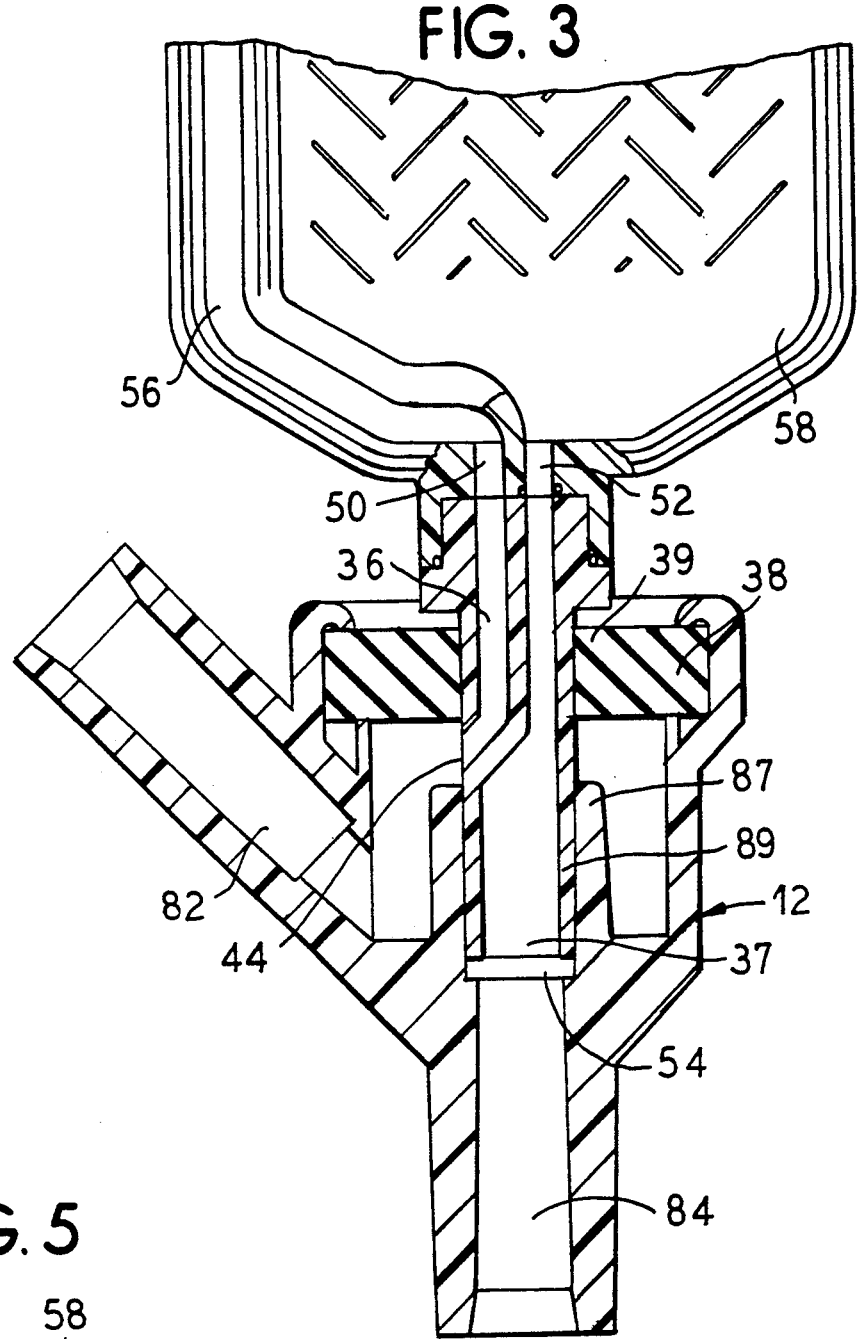
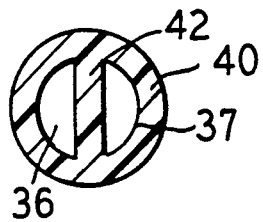
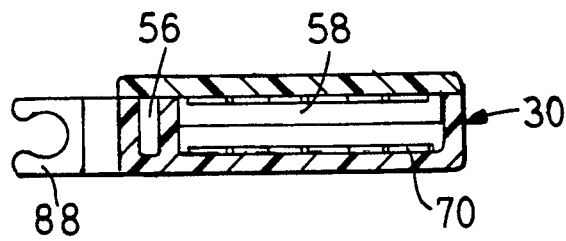

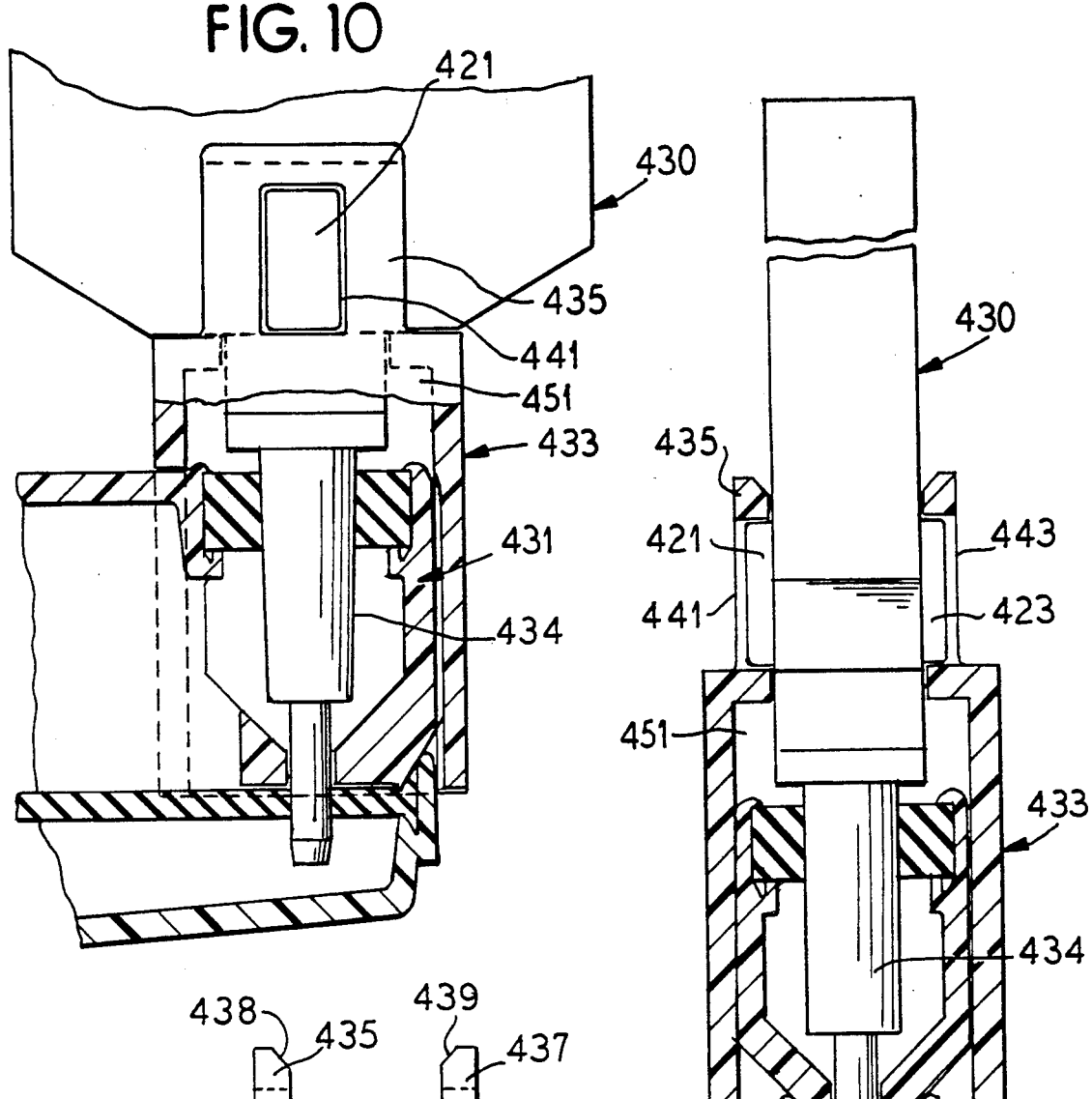
FIG. 10
FIG. 11
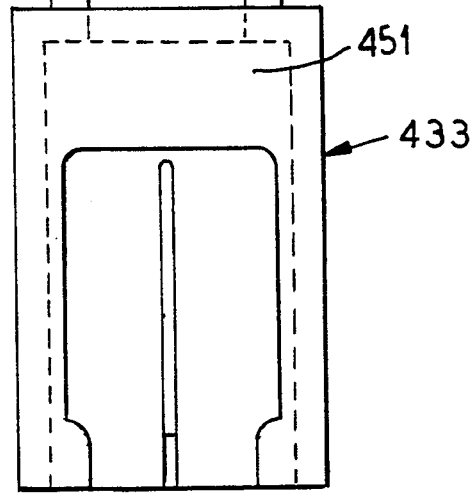
FIG. 12

CONTAINER FOR THE CONTROLLED ADMINISTRATION OF A BENEFICIAL AGENT

BACKGROUND OF THE INVENTION

The present invention relates to the delivery of beneficial agents within the fluid flow of a medical fluid. More specifically, the present invention relates to the control delivery into a fluid flow system of an agent that is dissolved so that it can become part of the fluid flow system.

It is known to parenterally deliver and collect medical fluids. Principally, these fluids are delivered, via an intravenous route or intraperitoneally. Examples of some intravenous fluids include blood and blood fractions, sugar, electrolytes, osmotic solutions, and nutrient preparations. Of course, many beneficial and therapeutic agents are delivered parenterally to avoid the digestive tract and liver. To this end, it is known to add medicaments and other agents to parenteral fluids for their intravenous administration.

Typically, these additional agents are added to a parenteral fluid reservoir by a pharmacist or a nurse. Because the addition of such agents is a labor intensive step, providing the opportunity for mistake and/or error, and further, since many beneficial agents are less stable in solution than in dry form, systems have been developed to facilitate formulation of soluble dry agents with parenteral fluid immediately before use.

Examples of systems to formulate parenteral fluid with soluble dry agents in situ in a formulation chamber associated with a primary delivery device include U.S. Pat. No. 4,552,555. Control delivery of a beneficial agent into a medical fluid can also be achieved through the diffusion of the agent from a non-erodible polymer matrix that contains and serves as a reservoir of the agent. Such systems are described in U.S. Pat. Nos. 3,921,636 and 4,511,353.

It is also known to provide a matrix that contains and/or protects, as necessary, one or more entrapped beneficial agents in a dry, stable state. The matrix, when placed in a flow chamber in a medical fluid administration line, disappears as the agent is delivered into the flowing stream, indicating delivery of the dose.

U.S. patent application Ser. No. 07/345,334, now abandoned entitled: "COMPOSITION AND METHOD FOR ADMINISTRATION OF BENEFICIAL AGENTS BY A CONTROLLED DISSOLUTION", assigned to the assignee of the instant patent application, provides an anhydrous, solid, water-soluble composition for the direct controlled administration of beneficial agents into a flow of medical fluid. The composition includes a matrix that is soluble in the medical fluid and in which the beneficial agent or agents are dispersed. Preferably, the matrix comprises one or more sugars or sugar alcohols in anhydrous solidified melt form. The beneficial agent or agents are distributed in particulate form and in predetermined patterns within the matrix. The beneficial agent can be carried in a conduit through which the medical solution passes. As the solution passes through the beneficial agent, a controlled amount of beneficial agent dissolves into each aliquot of medical solution which passes. The controlled amount per aliquot being substantially uniform for all the aliquots that pass from the first one to the last one.

An example of the use of the controlled administration of the beneficial agent is with respect to blood collected from a donor. As blood is collected from a donor, it passes into a container such as a blood bag which contains an anticoagulant system. Such anticoagulant systems typically include a small amount of liquid solution which is stored in the bag, usually ACD, CPD, CPD-adenine, or the like. In use with the controlled administration of the beneficial agent, the beneficial agent can be an anticoagulant/storage agent through which the blood passes on its way into a container.

U.S patent application Ser. No. 07/121,001, entitled: "AMPULE FOR CONTROLLED ADMINISTRATION OF BENEFICIAL AGENT" now U.S. Pat. No. 5,030,203 discloses a flexible ampule for use with a beneficial agent. The flexible ampule defines a pair of opposed, flexible sides sealingly enclosing a space which contains a mass of beneficial agent which is soluble in aqueous solution. Inlet and outlet ports communicate with the space and exterior of the ampule. Flow promoting means are positioned between the mass of beneficial agent at least one opposed, flexible side, to facilitate the formation of fluid flow paths along the path of the beneficial agent.

It is also known to provide in a set for the intravenous administration or other parenteral administration to a patient of a fluid solution a Y-site. The Y-site functions to provide a fluid flow path from a container to the patient while still allowing, via an injection site, a method for injecting or placing a second fluid or agent within the fluid flow path. To this end, the Y-site typically includes a tube extending from one arm of the Y-site and a tube extending from the bottom of the Y-site. The second arm of the Y-site includes an injection site. Fluid flows from the first arm of the injection site through the bottom of the Y-site into the second tube.

It is also known to provide in a set for parenteral administration a needleless injection site. An example of such a needleless injection site is disclosed in U.S. patent application Ser. No. 07/147,414, abandoned in favor of U.S. patent application Ser. No. 07/539,278, now issued as U.S. Pat. No. 5,188,620. The needleless injection site allows a blunt cannula to enter the injection site allowing the addition of a fluid or agent to the Y-site.

SUMMARY OF THE INVENTION

The present invention provides an improved means for delivering a beneficial agent to a fluid. To this end, in an embodiment, the invention provides a container for housing a solid beneficial agent. The housing comprises a body defining an interior including a chamber for housing the beneficial agent, the chamber having a first opening and a second opening. The interior also includes a channel extending along at least a portion of the perimeter of the chamber, that is separated by a wall for at least a portion of its length from the chamber. The channel at a first end is in fluid communication with the first opening and at a second end terminating in a channel opening. The container includes a member extending from a bottom of the body that defines a first and a second fluid flow path. The first fluid flow path is in fluid communication with the channel opening and the second fluid flow path is in fluid communication with the second opening of the chamber. The first and second fluid flow paths are separated by a wall from each other and terminate in separate openings in fluid communication with an environment outside the container.

In an embodiment, the invention provides a container for housing a beneficial agent that can be removably coupled to a structure defining a fluid flow path. The container comprises a body defining a first and second interior area, separated by a wall that terminates at an opening providing fluid communication between the first and second interior area. Means are provided that extend from the body for being removably received by the structure defining the fluid path. The means extending from the housing include an inlet opening and inlet fluid flow path and an outlet opening and outlet fluid flow path. The inlet fluid flow path being in fluid communication with the first interior area, and the outlet fluid flow path being in fluid communication with the second interior area. The second interior area includes means for housing the solid beneficial agent and means for causing fluid that flows through the inlet fluid flow path to pass by at least a portion of the solid beneficial agent.

In an embodiment, the second interior area of the container includes a plurality of raised grids.

In an embodiment, the body of the container includes means for removably securing the container to a portion of the housing defining a fluid flow path.

In an embodiment, the outlet opening is located at an end of the means extending from the body and the inlet opening is located between the end of the means and the body.

In a further embodiment, the present invention provides a container for housing a solid beneficial agent and for being removably coupled to a Y-site defining an inlet channel, an outlet channel, and a needleless injection site. The container comprises a body defining a channel and a chamber separated by a wall that terminates at an opening providing fluid communication between the channel and chamber, the chamber housing the solid beneficial agent. A cannula extending from the body for being removably received within the needleless injection site is provided. The cannula defining an inlet opening and inlet fluid path, and an outlet opening and outlet fluid path; the inlet fluid path being in fluid communication with the channel and the outlet fluid path being in fluid communication with the chamber. The cannula is so constructed and arranged that when it is received within the needleless injection site, the inlet opening is in fluid communication with the inlet channel and the outlet opening is in fluid communication with the outlet channel but not the inlet channel.

Additional features and advantages of the present invention are described in, and will be apparent from, the detailed description of the presently preferred embodiments and from the drawings.

BRIEF DESCRIPTION OF THE DRAWINGS

FIG. 1 illustrates a perspective view of the container of the present invention inserted within a Y-site of a fluid set.

FIG. 2 illustrates an enlarged view of the container of the present invention and a Y-site, prior to insertion of the container into the Y-site.

FIG. 3 illustrates an enlarged cross-sectional view of the container inserted in a Y-site.

FIG. 4 illustrates a cross-sectional view of the cannula of the container of FIG. 2 taken along lines IV—IV of FIG. 2.

FIG. 5 illustrates a cross-sectional view of a top portion of the container of FIG. 2 taken along lines V—V of FIG. 2.

FIG. 10 illustrates a cross-sectional view of a portion of a still further embodiment of the container and docketing site.

FIG. 11 illustrates a side elevational view of the embodiment of FIG. 10.

FIG. 12 illustrates the locating housing of FIG. 10.

DETAILED DESCRIPTION OF THE PRESENTLY PREFERRED EMBODIMENTS

Figure 6:
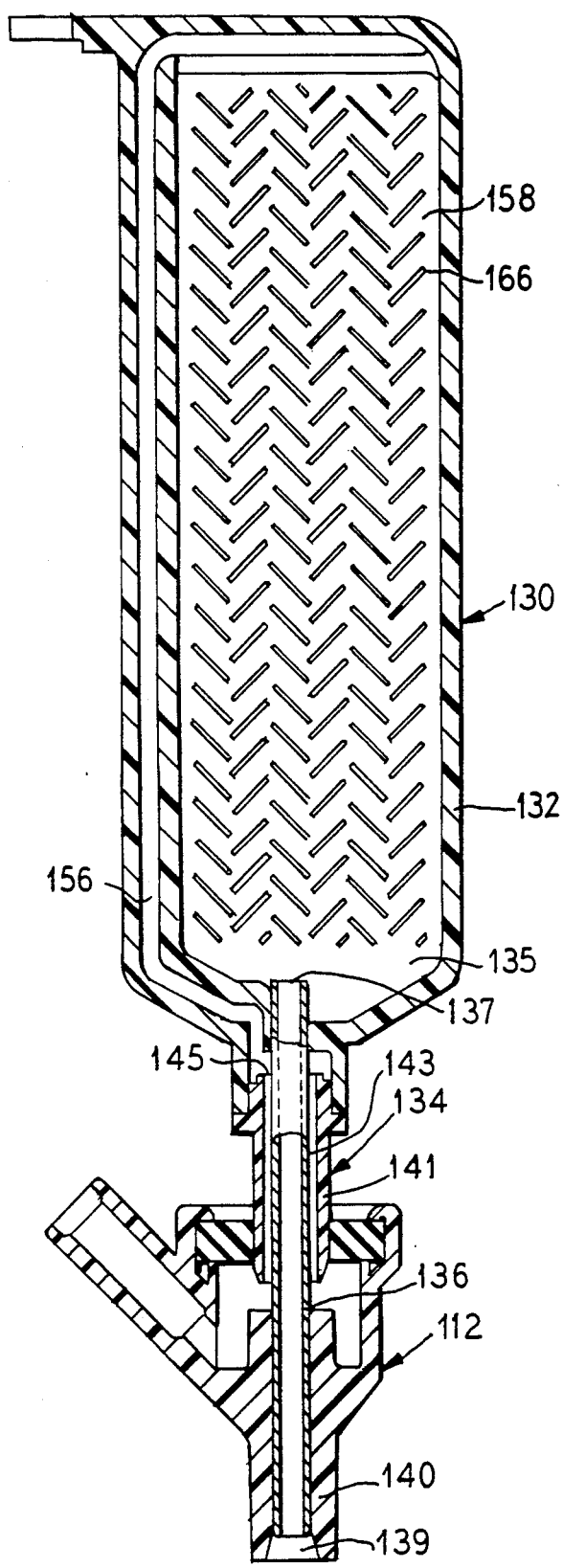
FIG. 6 illustrates a cross-sectional view of an embodiment of the container of the present invention docketing with an injection site.

The present invention provides a housing for a solid beneficial agent to be dissolved in a medical fluid. In an embodiment, the container of the present invention is specifically constructed so that it can be connected to a Y-site of an intravenous fluid communication set. Due to the construction of the container, fluid fed through the set will flow through the container dissolving the solid beneficial agent into the fluid.

Referring now to FIG. 1, a perspective view of a set 10 for the infusion of a liquid into a patient or from a patient into a container is illustrated. It should be appreciated that although a specific set is illustrated, as illustrated in the other figures, the container of the present invention can be used in other sets and with other structures.

In the set illustrated, a first fluid tube 11 is provided that is connected to a Y-site 12 that terminates in a further fluid tube 14. For example, the set 10 can be utilized to infuse a parenteral solution housed in the container (not shown) into a patient (not shown). In the illustrated set, the first fluid tube 11 is connected to a female luer 16, having a porous plug. The fluid tube 14 is connected to an inline filter 18, for eliminating air, that is connected to a third fluid tube 20 that terminates in a male luer 22.

As previously discussed, it may be desirable to add a beneficial agent to the fluid. One means for providing a beneficial agent to a fluid is to utilize the container 30 of the instant invention. As discussed in more detail hereinafter, the container 30 is constructed so that it can be removably coupled to a set, such as the set 10 illustrated.

Referring now to FIG. 2, the container 30 is illustrated prior to its insertion into the Y-site 12. The container 30 includes a body 32 that defines an interior 35. Preferably, the body 32 is constructed from a substantially rigid, clear plastic material.

Connected to a bottom end 33 of the body 32 is a cannula 34. As discussed in more detail hereinafter, the cannula 34 provides an inlet flow path 36 and an outlet flow path 37 from the container 30. The cannula 34 is designed to be received within the injection site 38 of the Y-site 12.

As illustrated in FIGS. 2, 3, and 4, the cannula 34 includes an outer tubular wall 40 that defines an interior that is divided by a wall 42. An inlet opening 44 is provided on a side 46 of the cannula 34. The inlet fluid flow path 36 extends from the inlet opening 44 to an opening 50 in the body 32. The outlet fluid flow path 37 extends from an outlet opening 52 in the body 32 to the outlet opening 54. The inlet fluid path 36 and outlet fluid path 37 are so constructed and arranged that there is no fluid communication directly between the paths. Fluid entering the inlet fluid path 36 must pass through the interior 34 of the body 32 of the container 30 prior to exiting the outlet opening 54 of the cannula 34. As discussed in more detail hereinafter, the cannula 34 is designed to be received in the Y-site 12 to create a fluid flow through the container 30.

The body 32 defines a channel 56 and a chamber 58 within the interior 35 thereof. To this end, a wall 60 is provided within the interior of the body 32 that defines a channel 56 that extends from the inlet opening 50 of the body 32 to an opening 62 in fluid communication with a portion of the chamber 58. The channel 56 provides an inlet fluid path 64 within the body 32 of the container 30. Fluid that enters the inlet opening 44 of the cannula 34 is fed through the inlet fluid path 36 of the cannula 34 through the channel 56 within the interior 34 of the body 32.

The channel 56 terminates at an opening 62 in fluid communication with the chamber 58. Accordingly, fluid that flows through the fluid path 64 defined by the channel 56 enters the chamber 58 at the opening 62.

The chamber 58 is so constructed and arranged to receive a solid beneficial agent 66. Because of the construction of the body 32, fluid that enters the inlet 44 of the cannula 34 and passes through the channel 56 is fed over the beneficial agent 66 located within the chamber 58.

As used herein, solid beneficial agent 66 refers to an at least substantially solid composition. Examples of such masses of beneficial agent 66 are set forth in U.S. patent application Ser. No. 07/345,334, now abandoned, entitled: "COMPOSITION AND METHOD FOR THE ADMINISTRATION OF BENEFICIAL AGENTS BY CONTROLLED DISSOLUTION". Briefly, the solid beneficial agent comprises an anhydrous, solid, water-soluble composition that allows the direct controlled administration of beneficial agents to a flow of medical fluid. To this end, the composition includes a matrix that is soluble in the medical fluid and in which the beneficial agent or agents are dispersed.

In an embodiment, the matrix comprises one or more sugars or sugar alcohols in an anhydrous solidified melt form. The beneficial agent or agents are distributed in particulate form and in a predetermined pattern within the matrix. For example, the solid beneficial agent can be utilized to simplify the parenteral administration of: water insoluble beneficial agents; activated beneficial agents; beneficial agents in modified or modulating agents in predetermined, concurrent and/or sequential manner; easily inactivated beneficial agents; and a beneficial agent and its inactivator or its antagonist released sequentially.

Preferably, the beneficial agent is in the form of a unitary mass, for example, a tablet of glassy material. For example, the tablet of glassy material can comprise at least one material from the group consisting of sugar and a water soluble, non-toxic citrate, such as sodium citrate or citric acid. The use of a substantially dry mass of beneficial agent, positioned within the chamber in accordance with this invention provides significant advantages. In a preferred embodiment, the container 30 is designed to provide a chamber 58 for accommodating a glass tablet having a construction of approximately 2½ inches long by 3¼ inches wide and 0.100 inches thick.

As the fluid from the channel 56 is passed over the solid beneficial agent 66, the solution dissolves a portion of the solid beneficial agent 66. Therefore, the fluid that exits the chamber 58 through opening 52 into the outlet fluid path 37 of the cannula not only contains the fluid fed within the inlet opening 44, but additionally, contains at least some of the beneficial agent contained within the solid mass.

Due to the construction of the container 30, incoming solution is automatically routed to a top 68 of the body 32 and into the chamber 58 past the solid beneficial agent 66. After passing by the solid beneficial agent 66, the fluid is routed out of the housing 32 downstream. Due to the construction of the cannula 34, the flow path does not allow any mixing of inlet (drug free) and outlet (dissolved drug) solutions.

Energy directors can be provided in the housing of the container, for example, in the perimeter of the bottom housing and between the channel and chamber for providing a better mixing of fluid and agent.

In an embodiment, the chamber 58 includes a raised grid pattern 70 molded into the surface of the interior of the body 32. The grid pattern 70 provides a consistent solution flow path at the solid beneficial agent 66 surface. This therefore insures a uniform dissolution of the agent into the solution.

As previously stated, in a preferred embodiment, the container 30 is specifically designed to be received within an injection site 38 of a Y-site 12. In the preferred embodiment illustrated, the container 30 is designed to be received within a needleless injection site 38 that includes a preslit member 39 which is designed to receive the cannula 34.

The cannula 34 is so constructed and arranged that when it is received within the injection site 38, fluid communication is established between the inlet opening 44 of the cannula 34 and the inlet fluid flow path 82 of the Y-site 12. At the same time, fluid communication is established between the outlet opening 54 of the cannula 34 and the outlet fluid flow 84 path of the Y-site 12. However, fluid communication is not established between the inlet opening 44 of the cannula 34 and the outlet fluid path 84 of the Y-site 12 and the outlet opening 54 of the cannula 34 and the inlet fluid flow path 82 of the Y-site 12. Therefore, solution is fed through the inlet flow path 82 of the Y-site 12 into the inlet opening 44 of the cannula 34 and through the channel 56 into the interior 35 of the container 32. The fluid is then passed over the solid beneficial agent 66 located in the chamber 58. Fluid then exits the outlet 54 of the cannula 34 and flows into the outlet fluid flow path 84 of the Y-site 12. Accordingly, fluid that exits the outlet opening 54 of the cannula 34 includes some beneficial agent contained within the solid beneficial agent 66 located within chamber 58.

To achieve the desired fluid flow paths, in the embodiment illustrated in FIGS. 3 and 4, the Y-site includes an extending interior member 87. A portion 89 of the cannula 34 is designed to be received within the interior member 87 separating the fluid paths.

The container 30 of the present invention provides a design that requires the user to make only one connection when connecting the container of the present invention that includes the beneficial agent into an intravenous extension set. Although the container 30 is designed for one-time use, the needleless access injection Y-site 38 is designed for multiple uses. The container of the present invention provides an easy means for removably connecting the container to the Y-site 12.

As illustrated in FIG. 5, in the preferred embodiment of the container 30 illustrated, a coupling member 88 is provided for coupling the container 30 to a tube 11 of the set 10. Once the cannula 34 is received within the Y-site 12, the coupling member 88 can be coupled to the tube 11 to provide a stable connection of the container 32 to the set 10.

FIG. 6 illustrates a further embodiment of the container 130 of the present invention. Again, the container 130 provides a housing for allowing a solid beneficial agent 166 to be dissolved in a medical fluid. To this end, the housing defines a chamber 158 for housing the agent 166. Within the chamber 158 a similar fluid flow path is provided as in the previous embodiments. However, as compared to the embodiment of the invention illustrated in FIGS. 1-5, a different cannula structure 134 is utilized.

The cannula 134 has a construction substantially similar to that illustrated in U.S. Pat. No. 4,850,978, the disclosure of which is incorporated herein by reference.

Briefly, the cannula 134 includes a tube member 136 that terminates at an opening 137 located in the interior 135 of the body 132 of the container 130. The cannula 134 defines a fluid path from the outlet portion of the body 132 and an opening 139 at an end 140 of the tube 136.

The cannula 134 includes a shell 141 that circumscribes a portion of the tube 136 and defines therebetween a channel 143. The channel 143 provides fluid communication between an opening 145 and the channel 156 of the container 130.

The cannula 134 is designed to dock, for example, with an injection site 112. The injection site 112 is similar to the injection site illustrated in FIG. 3 and cooperates with the cannula 134 so that a flow path is created similar to that described with respect to FIG. 3.

Figure 7:
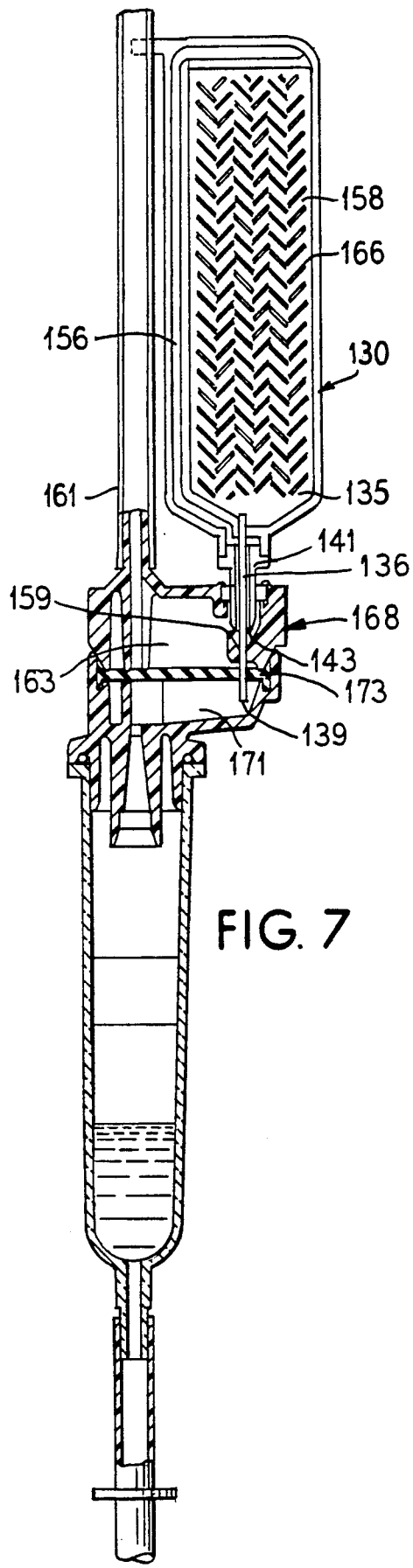
FIG. 7 illustrates a cross-sectional view of the container of FIG. 6 docketing with a further embodiment of an injection site.

FIG. 7 illustrates the docketing of the cannula 134 with a further embodiment of an injection site 168. This injection site is similar to an injection site disclosed in U.S. Pat. No. 4,850,978. Briefly, when the cannula 134 is so received in the injection site 168, fluid flow is established with respect to chamber 158 and a fluid path defined within the tube 136 and between the channel 156 and a fluid path defined between the tube 136 and shell 141.

In the injection site 168, fluid flows through tube 161 into an upper chamber 163 of the injection site 168. The upper chamber 163 is in fluid communication with an opening 159 of the channel 143 defined by the shell 141. This allows fluid to flow through the channel 143 into the channel 156 of the container 130. The fluid then flows over the agent and out of the tube 136.

The exit opening 139 of the tube 136 is in fluid communication with a lower chamber 171. A barrier 173 prevents fluid communication between the upper and lower chambers. From the lower chamber 171, the fluid can then flow, if desired, to the patient. The fluid that flows to the lower chamber 171, due to this construction, includes the beneficial agent.

Figure 8:
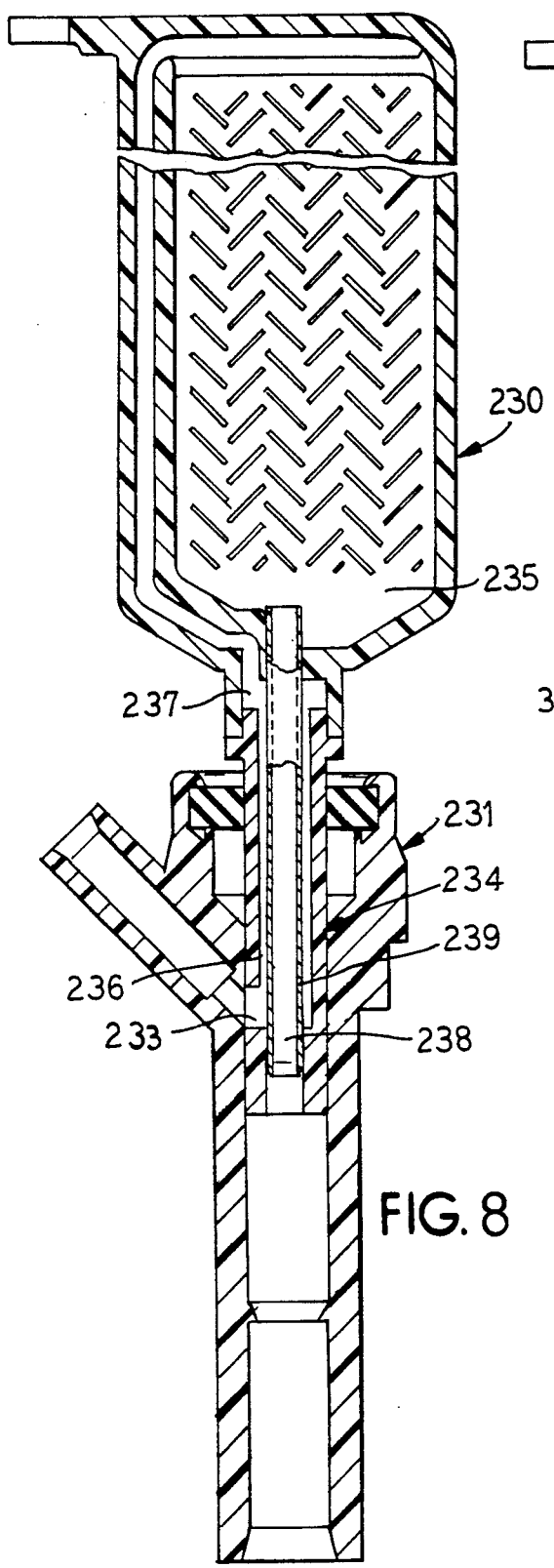
FIG. 8 illustrates a cross-sectional view of a further embodiment of the container of the present invention.

Referring now to FIG. 8, an embodiment of the device is illustrated wherein the cannula 234 is designed to be received within a universal InterLink ™ Y-site 231. The cannula 234 includes an opening 233 for providing fluid flow through a first path 236 into the inlet opening 237 of the container 230. A second fluid path 238 is defined, in the embodiment illustrated, by a tube 239 that extends from an interior 235 of container 230.

This construction of the cannula 234 will allow the cannula 234 and container 230 to dock with a universal InterLink ™ Y-site available from Baxter Healthcare Corporation. The InterLink ™ system includes a preslit resealable membrane that is designed to receive a blunt cannula. The InterLink ™ system is disclosed in U.S. patent application Ser. No. 07/147414 entitled , "Preslit Injection Site and Associated Cannula", abandoned in favor of U.S. patent application Ser. No. 07/539,278, now issued as U.S. Pat. No. 5,188,620, the disclosures of which are incorporated herein by reference.

Figure 9:
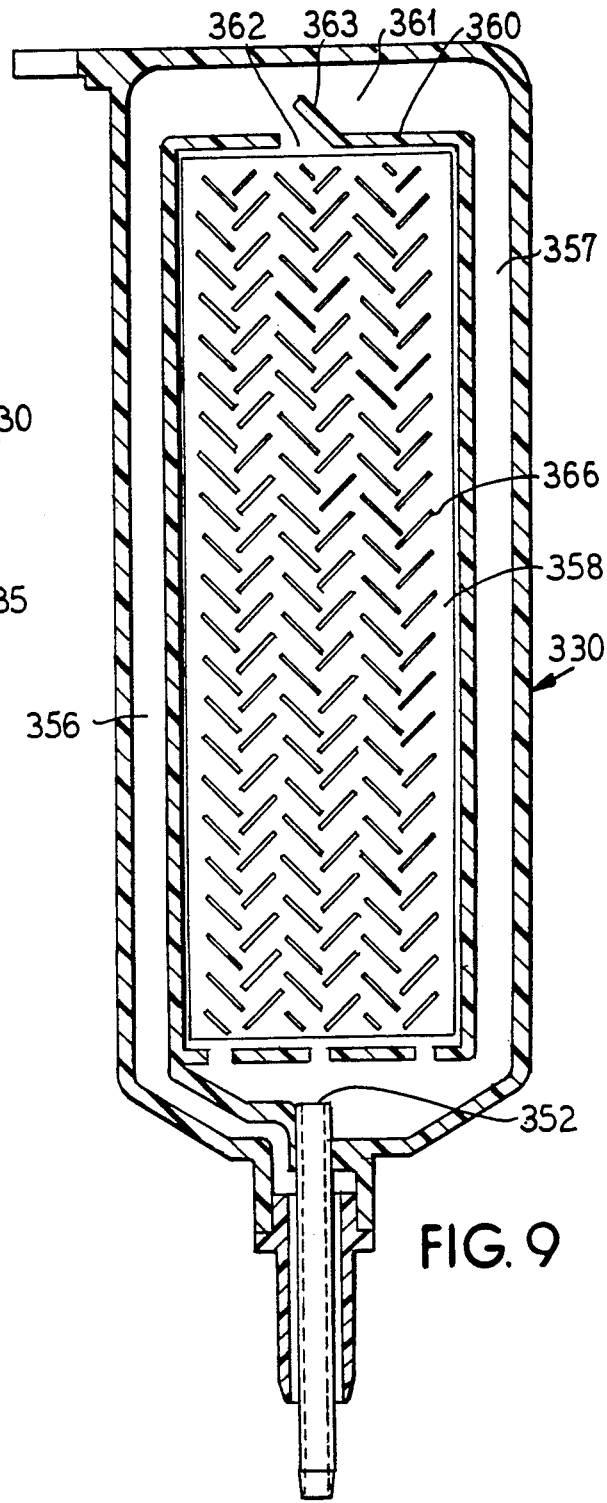
FIG. 9 illustrates a cross-sectional view of a further embodiment of the container of the present invention.

Referring now to FIG. 9, a further embodiment of the present invention is illustrated. In this illustrated embodiment, the container 330 is constructed so that the effective flow rate past the beneficial agent 366 can be reduced without reducing the total flow through the device. The dissolution of the beneficial agent 366 is dependent on the flow rate of solution past the matrix. For certain applications, extensions of delivery time, that can be achieved by reducing the flow rate, would be desirable.

With respect to the device illustrated in FIG. 9, the basic design illustrated in FIGS. 1-5 is utilized. However, two possible flow paths are provided which incoming fluid can traverse. A portion of the fluid will travel through the channel 356 into the chamber 358 and through the outlet 352. Alternatively, a portion of the fluid will travel through the channel 356 and through a second channel 357 and through the outlet path 352. To achieve the dual fluid path, a wall 360 is provided that extends across a portion of the top 361 of the container 330. The wall 360 includes an aperture 362 as well as a flange member 363 for directing at least a portion of the fluid into the chamber 358.

This design allows one to create the desired flow rate without requiring the practitioner to adjust the total intravenous flow to the patient. Further, this allows maintenance of normal IV fluid rates but allows one to limit the concentration of agent 366 that is delivered. Concentration of beneficial agent 366 could become excessive if one were merely to reduce the total flow rate through the chamber 358.

The ratio of fluid travelling to the separate fluid paths will be determined by the resistance to flow in each of the separate paths. The flow through either path will be inversely proportional to the magnitude of the resistance of that path.

The resistance of the flow path through the chamber 358 containing the beneficial agent 366 can be easily varied by changing the size of the aperture 362 by which the chamber 358 communicates with the fluid channel 356. Although a flange member 363 is illustrated, fluid divergence can also be achieved by a slot in the outer surface of the cannula itself or some other similar mechanism by which a portion of the fluid would be allowed to flow directly through the Y-site while another portion of the fluid will be diverted into the matrix chamber. Thus, a flow passed the matrix could be reduced without effecting the total flow of diluent through the system.

Referring now to FIGS. 10-12, a further embodiment of the present invention is illustrated. In this embodiment, again the principles of the invention set forth with reference to FIGS. 1-5 are utilized. However, this embodiment provides modifications to ensure proper docking of the container 430 with the injection site 431.

In this embodiment, the injection site 431 includes a locating housing 433, illustrated in FIG. 12. As illustrated in FIGS. 10 and 11, the locating housing 433 is designed to circumscribe a portion of the injection site 431 and includes legs 435 and 437 that extend therefrom. The legs 435 and 437 includes tapered portions 438 and 439, respectively. The tapered portins 438 and 439 cooperate to allow a portion of the container 430 to be received within the locating housing 433.

Additionally, the legs 435 and 437 include apertures 441 and 443. Correspondingly, two docking pads 421 and 423 are provided on the container 430 on opposite sides of the container. The locating housing 433 ensures that the cannula 434 is properly positioned with respect to the injection site 431 and received therein and allows the container 430 to be locked therein.

In this regard, in use, the container 430 is urged downwardly between the legs 435 and 437, allowing the cannula 434 to be received within an interior 451 of the locating housing 433. As the cannula 434 is so received, the docking pads 421 and 423 bias the legs 435 and 437 outwardly so as to allow the pads 421 and 423 to be received in the apertures 441 and 443 locking the container 430 in place. The locating housing 433 is so constructed and arranged that when the docking pads 421 and 423 are located within the apertures 441 and 443, the cannula 434 is properly docked with the injection site 431 and is locked in place. This concept can be utilized with any of the embodiments of the invention previously described.

The embodiment illustrated in FIGS. 10-12 ensures that the cannula 434 is properly located within the injection site 431. Further, the locating housing 433 provides a means for securely attaching the container 430 to the injection site 431. Additionally, the locating housing 431 adds protection against touch contamination of the cannula 434.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A container for housing a solid beneficial agent comprising:
    a body defining an interior including a chamber having a length for housing a solid beneficial agent, the chamber having a first opening and a second opening, the interior also including a channel defined by at least a portion of the body extending along at least a portion of the perimeter along the length of the chamber and being separated by a wall from the chamber for at least a portion of the length of the chamber, the channel at a first end being in fluid communication with the first opening and at a second end terminating in a channel opening; and
    a member extending from a bottom of the body and defining a first fluid flow path and a second fluid flow path, the first fluid flow path being in fluid communication with the first opening and the second fluid flow path being in fluid communication with the second opening of the chamber, the first and second fluid flow paths being separated by a wall from each other and terminating in separate openings in fluid communications with an environment outside the container.

2. The container of claim 1 wherein the channel extends for a majority of a length of the body.

3. The container of claim 1 including means for removably securing the container to an object.

4. The container of claim 1 wherein the body is constructed form a substantially clear plastic.

5. The container of claim 1 wherein the interior of the chamber includes a raised grid pattern.

6. The container of claim 1 wherein the body includes means for diverting at least a portion of fluid from flowing into the chamber.

7. The container of claim 1 wherein the body defines a third fluid flow path, the third fluid flow path extending from the first fluid flow path and terminating at a third opening in fluid communications with the outside environment.

8. The container of claim 1 wherein the body includes on an outer surface thereof at least one docking pad.

9. A container for housing a solid beneficial agent and being removably coupled to a housing defining a fluid flow path comprising:
    a body having a length defining a first interior area and a second interior area separated by a wall that terminates at an opening providing fluid communication between the first interior area and the second interior area wherein the wall extends substantially parallel to the length of the body and further extends for a majority of the length of the body;
    means extending from the body for being removably received by a housing defining a fluid flow path, the means extending from the body including an inlet opening and an inlet fluid flow path and an outlet opening and an outlet fluid flow path wherein the inlet fluid flow path is in fluid communication with the first interior area, and the outlet fluid flow path is in fluid communication with the second interior area; and
    the second interior area including means for containing the solid beneficial agent and means for causing fluid that flows through the inlet fluid flow path to pass by at least a portion of the solid beneficial agent.

10. The container of claim 9 wherein the body includes means for diverting at least a portion of the fluid from flowing into the chamber.

11. The container of claim 10 further comprising a third interior area separated by a wall form a portion of the second area within the body and in fluid communications with said first and second interior areas of the body.

12. The container of claim 9 wherein the body is constructed form a substantially rigid clear plastic.

13. The container of claim 9 wherein the second interior area includes a plurality of raised grids.

14. The container of claim 9 wherein the body includes means for removably securing the container to a portion of the housing defining a fluid flow path.

15. The container of claim 9 wherein the outlet opening is located at an end of the means extending from the body and the inlet opening is located between the end of the means extending from the body and the body.

16. The container of claim 9 wherein the means extending from the body includes a cannula.

17. The container of claim 9 wherein the means extending from the body includes a blunt cannula.

18. The container of claim 9 wherein the body includes on an outer surface thereof at least one docking pad.

19. The container of claim 9 wherein the housing defining the fluid flow path is a Y-site.

20. A container for being removably coupled to a Y-site defining an inlet channel, an outlet channel, and a needleless injection site, comprising:
a body defining a channel and a chamber having a length separated by a wall that terminates at an opening providing fluid communication between the channel and the chamber, the chamber housing a solid beneficial agent and the channel extending along at least a portion of the perimeter along the length of the chamber; and
a cannula extending rom the body for being removably received within the needleless injection site of the Y-site and defining an inlet opening and an inlet fluid path, and an outlet opening and an outlet fluid path, the inlet fluid path being in fluid communication with the channel of the body and the outlet fluid path being in fluid communication with the chamber, the cannula being so constructed and arranged that when it is received within the needleless injection site, the inlet opening is in fluid communication with the inlet channel of the Y-site and the outlet opening is in fluid communication with the outlet channel of the Y-site but not the inlet channel of the Y-site.

21. The container of claim 20 wherein the body includes means for diverting at least a portion of the fluid from flowing into the chamber.

22. The container of claim 21 wherein the means includes a third interior area separated by a wall from a portion of the chamber area.

23. The container of claim 20 wherein the chamber includes a plurality of grids.

24. The container of claim 20 wherein the inlet opening is located between the body and an end of the cannula.

25. The container of claim 20 wherein the outlet opening is located at an end of the cannula.

26. The container of claim 20 including means for removably coupling the body to a tube connected to the Y-site.

27. The container of claim 20 wherein the body includes on an outer surface thereof at least one docking pad.

28. The container of claim 20 wherein the body is constructed from a substantially rigid clear plastic.

29. The container of claim 20 further comprising:
an interior portion extending from the Y-site for receiving a portion of the cannula when the cannula is received in the injection site.

* * * * *

UNITED STATES PATENT AND TRADEMARK OFFICE
CERTIFICATE OF CORRECTION

PATENT NO.   : 5,304,130
DATED        : April 19, 1994
INVENTOR(S)  : Kathryn M. Button et al.

It is certified that error appears in the above-indentified patent and that said Letters Patent is hereby corrected as shown below:

In Claim 20, column 11, line 17, "rom" should be --from--

Signed and Sealed this

Second Day of May, 1995

Attest:

BRUCE LEHMAN

Attesting Officer

Commissioner of Patents and Trademarks